(12) United States Patent
Hickle

(10) Patent No.: US 6,962,564 B2
(45) Date of Patent: Nov. 8, 2005

(54) SYSTEMS AND METHODS FOR PROVIDING GASTROINTESTINAL PAIN MANAGEMENT

(76) Inventor: Randall S. Hickle, 2404 Topeka Ave., Lubbock, TX (US) 79407

( * ) Notice: Subject to any disclaimer, the term of this patent is extended or adjusted under 35 U.S.C. 154(b) by 0 days.

(21) Appl. No.: 10/724,871

(22) Filed: Dec. 2, 2003

(65) Prior Publication Data

US 2004/0152949 A1 Aug. 5, 2004

Related U.S. Application Data

(60) Provisional application No. 60/430,055, filed on Dec. 2, 2002.

(51) Int. Cl.$^7$ ................................................ A61B 1/04
(52) U.S. Cl. ..................... 600/114; 600/127; 600/115; 600/116
(58) Field of Search ........................ 600/127, 114–116, 600/104, 153, 156, 129; 604/512

(56) References Cited

U.S. PATENT DOCUMENTS

| | | |
|---|---|---|
| 5,183,031 A | 2/1993 | Rossoff |
| 5,579,758 A | 12/1996 | Century |
| 5,817,073 A | 10/1998 | Krespi |
| 5,913,816 A | 6/1999 | Sanders et al. |
| 6,027,499 A | 2/2000 | Johnston et al. |
| 6,224,544 B1 | 5/2001 | Takada |
| 6,599,237 B1 * | 7/2003 | Singh ........................ 600/114 |
| 6,645,140 B2 * | 11/2003 | Brommersma .............. 600/128 |
| 2001/0012923 A1 | 8/2001 | Christopher |
| 2002/0049365 A1 | 4/2002 | Takada |

* cited by examiner

Primary Examiner—Beverly M. Flanagan

(57) ABSTRACT

The present invention includes systems and methods for decreasing the pain and discomfort commonly associated with endoscopic procedures, where such procedures may be performed with lower dosage levels of sedative and analgesic drugs. The invention includes use of an anesthetic collar coupled to an endoscope with a flexible shaft. The anesthetic collar allows lubricants, local anesthetics, dyes, and/or other desirable fluids to be passed through the existing lumen of the flexible shaft into an annulus, where the fluid may be distributed through expulsion pores into the gastrointestinal tract. Utilizing the existing lumens found in endoscopes, the present invention allows those fluids that may reduce the pain and discomfort associated with endoscopies such as, for example, local anesthetics and lubricants, to be distributed in an even fashion throughout the gastrointestinal tract or throughout the length and circumference of the endoscope, where such fluids may reduce the drug level requirements for sedative and analgesic agents. Alternatively, the endoscope may be redesigned for streamlined integration with the anesthetic collar or to accomplish the same function of distributing local anesthetics and lubricants, in an even fashion throughout the gastrointestinal tract or throughout the length and circumference of the endoscope, The invention can also be used with endoscopes without existing lumens.

24 Claims, 9 Drawing Sheets

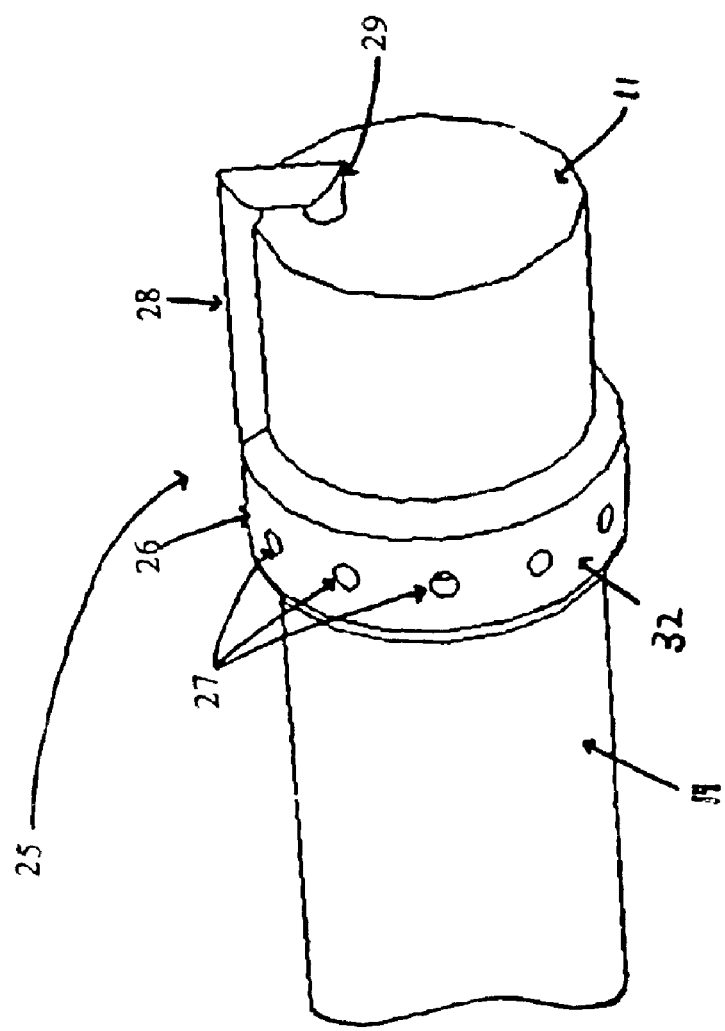

SYSTEMS AND METHODS FOR PROVIDING GASTROINTESTINAL PAIN MANAGEMENT

CROSS REFERENCE TO RELATED APPLICATIONS

This application claims priority under 35 U.S.C. §119(e) to U.S. Provisional Patent Application No. 60/430,055, "Systems and Methods for Providing Gastrointestinal Pain Management," filed Dec. 2, 2002, which is hereby incorporated by reference.

STATEMENT REGARDING FEDERALLY SPONSORED RESEARCH OR DEVELOPMENT

Not Applicable

REFERENCE TO A "MICROFICHE APPENDIX"

Not Applicable

BACKGROUND OF THE INVENTION

1. Field of the Invention

The present invention relates, in general, to systems and methods of medical pain management and, more particularly, to the management of pain and discomfort associated with endoscopies.

2. Description of the Related Art

Endoscopy is a term used to describe medical procedures involving the use of an endoscope, where an endoscope is an instrument for examining visually the interior of a bodily cavity or a hollow organ such as the colon, bladder, or stomach. Endoscopic procedures include colonoscopies, esophagogastroduodenoscopies (EGDs), and other visually invasive procedures, where a number of fiber optic and video chip endoscopes have been specifically designed and adapted to particular areas of operation.

Colonoscopies and other procedures involving the insertion of an endoscope into the colon of a patient are generally performed using sedation administered intravenously with medications such as benzodiazepine sedatives (Midazolam) and/or opioid narcotic analgesics (Fentanyl). Undesirable effects of IV sedation drugs for a patient may include, among others, respiratory depression, missed work due to time of recovery from drug effect, and anaphylaxis or other allergic reactions. The pain and discomfort of endoscopies are generally attributable to the stimulation of pain sensitive nerve endings found in the mucous membranes of the gastrointestinal tract. In attempts to alleviate the pain and discomfort in the absence of sedatives, oral and rectal local anesthetic sprays have been developed that deliver lidocaine and other local anesthetic agents to a particularly sensitive region. These agents may have only a nominal affect on the pain and discomfort experienced by the patient as the endoscope is driven farther into the gastrointestinal tract.

Colonoscopy is a generic term describing the common procedure employed in examining the colon with a fiber optic system which is known as a colonoscope. The colonoscope is also used in removing polyps and other tissue in the colon for diagnostic and other purposes.

During an examination, the colonoscope (or endoscope) is driven into the rectum, through the sigmoid colon and the descending colon into the splenic flexure. At this point, the scope must be manipulated through a ninety-degree bend to enter the transverse colon. While colonoscopes generally have a steerable or bendable head, the force necessary to progress the colonoscope across the splenic flexure can only be applied by pushing the colonoscope from outside the anus in a direction at right angles to the desired direction of travel. After the colonoscope has moved through the transverse colon, the colonoscope encounters the hepatic flexure, another ninety-degree turn leading to the ascending colon. To steer the scope down the ascending colon toward the caecum, force applied to the portion of the colonoscope located near the anus of the patient must vector through a minimum of two right angle bends.

The manipulations used to move the colonoscope through the rectum and colon may be extremely painful and uncomfortable to the patient due to the nerve endings in the colon located in the mucosal and muscular walls. The principal forces to which these nerves are sensitive are stretching and tension, both of which occur when the relatively rigid colonoscope passes through the colon. In general, the only existing means of relieving the pain and discomfort that result from the stretching, torsion, and friction incurred during a colonoscopy is to provide sedation and analgesia to the patient, an often undesirable alternative since the drug levels required to relieve the discomfort often render the patient unable to cooperate during the procedure.

In the past, attempts have been made to make endoscopic devices such as gastric tubes and catheters pass more easily through tubular body structures by coating them with polymers having low coefficients of friction. Such coatings must be bonded to the device, either covalently or by other means. These coatings are subject to wear and eventually can lose their effectiveness, particularly when applied to reusable devices such as colonoscopes and cystoscopes. Permanent coatings also must be able to withstand sterilization and/or disinfecting procedures without losing effectiveness, a difficult technical requirement.

Endoscopic devices have also been coated with a petrolatum or water-based lubricant prior to insertion as a means of easing patient discomfort. However, in the case of colonoscopy, these lubricants are often removed from the colonoscope as it is inserted into the rectum and advanced through the anal sphincter. Very little lubricant remains afterwards to ease further manipulation of the colonoscope. Certain existing devices attempt to reduce the amount of lubricant and anesthetic lost during insertion of the colonoscope by employing a syringe or flexible plastic bottle equipped with a long applicator tip to coat the surface of the colonoscope while the colonoscope passes through the rectum. Though such devices may have some effect in reducing the friction coefficient of the colonoscope, much of the lubricant and/or anesthetic may be lost as the colonoscope is pushed farther into the colon. Further, applying the lubricant and/or anesthetic to the colonoscope inside the rectum may make fully coating the scope and fully coating sensitive colon tissue a difficult task.

BRIEF SUMMARY OF THE PRESENT INVENTION

The present invention includes systems and methods for decreasing the pain and discomfort commonly associated with endoscopic procedures, where such procedures may be performed with lower dosage levels of sedative and analgesic drugs. The decreased requirements for sedative and analgesic drugs allow the patient to remain conscious and able to participate in the procedure. The systems and methods of the present invention further permit the easy sterilization and effective reuse of expensive medical equipment and the delivery of an anesthetic and/or lubricant at a consistent level of effectiveness, concentration, and coverage as the colonoscope is pushed farther into the colon. The invention further comprises systems that deliver the anesthetic and/or lubricant in a consistent manner, where the anesthetic and/or lubricant may be applied to all desired gastrointestinal areas in a comprehensive and effective manner. A less painful endoscopic procedure may diminish the need for heavy sedation thus reducing the likelihood of unintended loss of consciousness during endoscopic procedures that are inherently painful.

BRIEF DESCRIPTION OF THE DRAWINGS

FIG. 2A illustrates one embodiment of an anesthetic collar with an adapter for delivering fluid to a patient's gastrointestinal tract in accordance with the present invention;

DETAILED DESCRIPTION OF THE INVENTION

Figure 1:
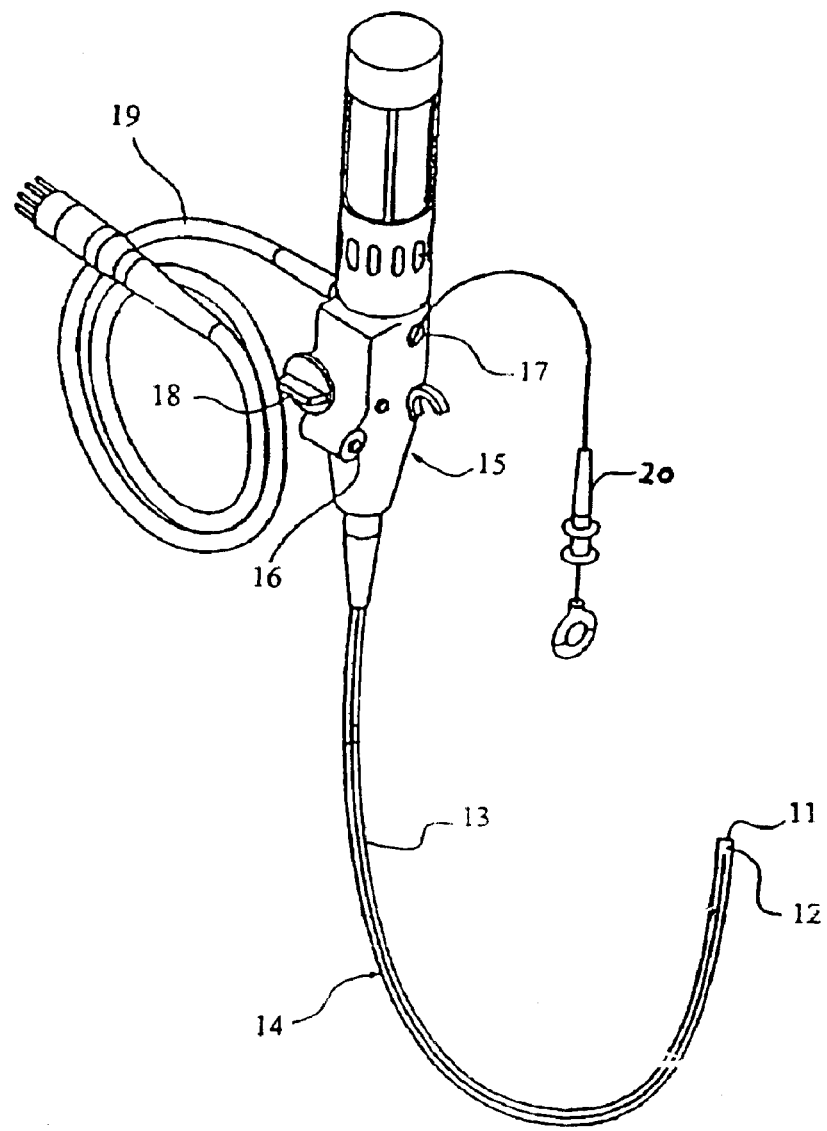
FIG. 1 illustrates one embodiment of an endoscopic scope for use with the present invention.
Figure 5:
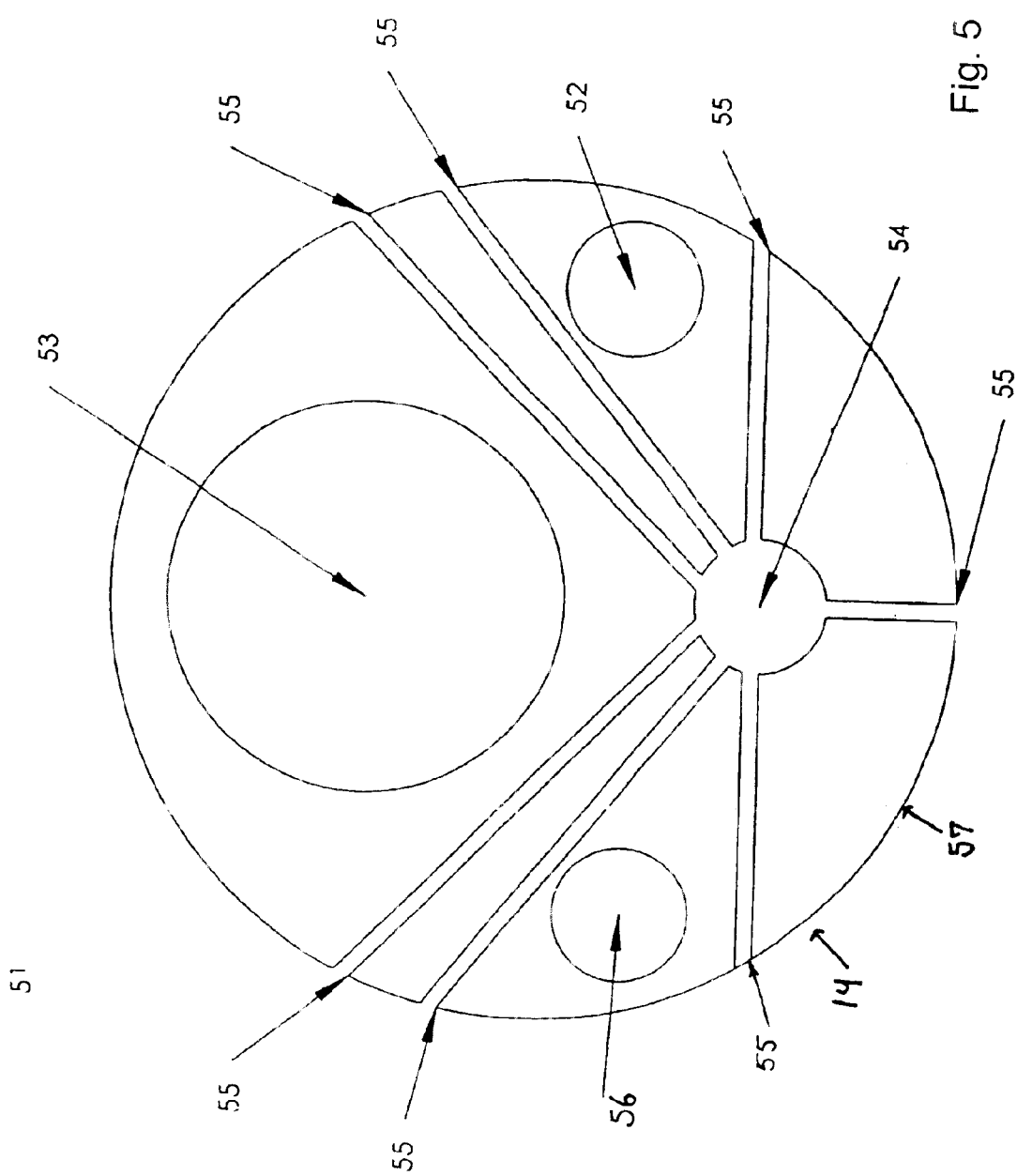
FIG. 5 illustrates a cross-sectional view of the flexible shaft of an endoscope having a fluid delivery system in accordance with the present invention.
Figure 6:
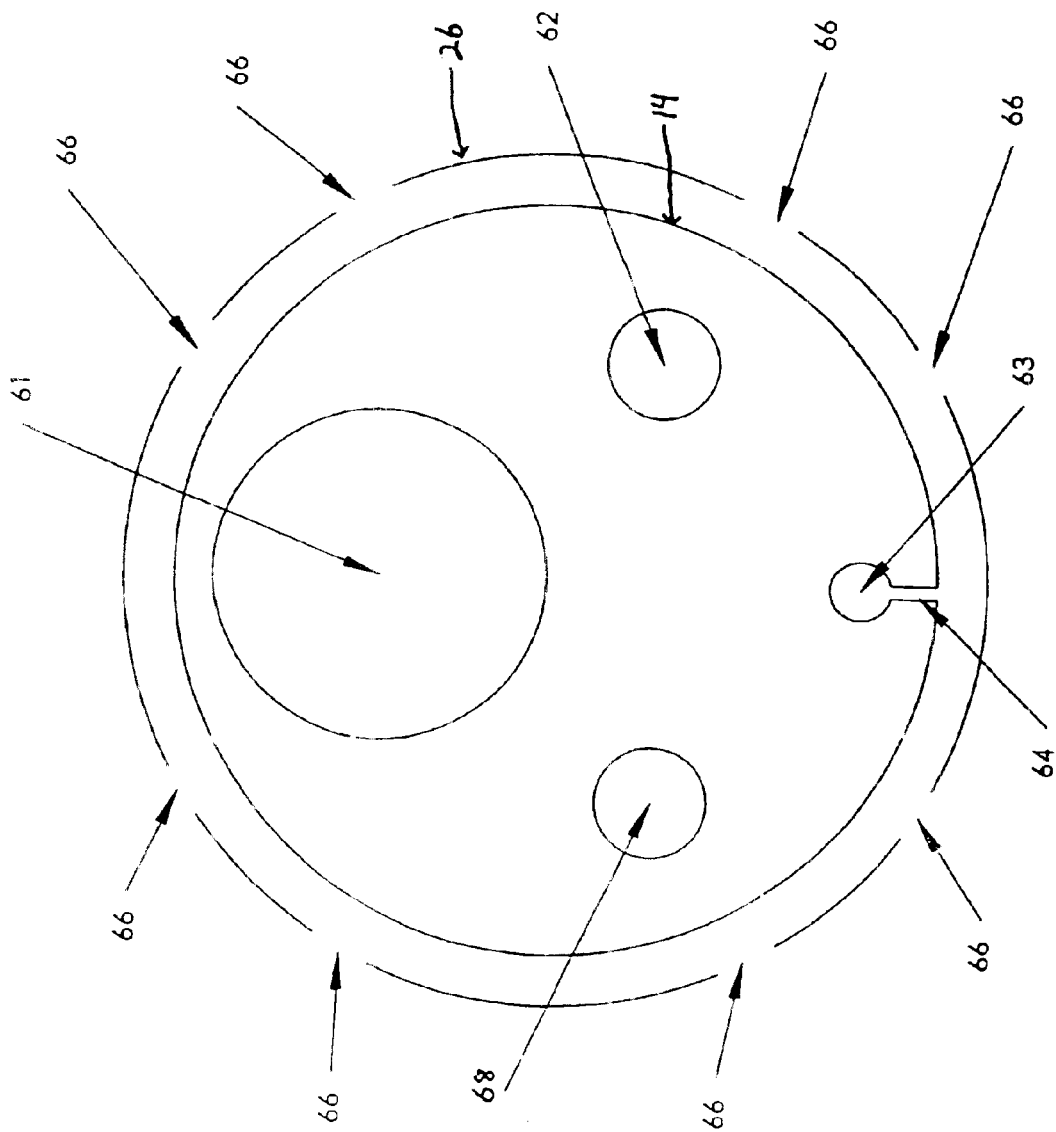
FIG. 6 illustrates a cross-sectional view of the flexible shaft of an endoscope having an annulus and a fluid delivery system in accordance with the present invention.

FIG. 1 shows an endoscope 10 having distally a flexible shaft 14 and proximally an operating unit 15. Flexible shaft 14 comprises a distal section 11, a bending section 12, and a flexible section 13. The bending section 12 may be flexed in all directions by adjusting a control knob 18, mounted at operating unit 15. The distal section 11 of flexible shaft 14 may be provided with image receiving windows, light projecting windows, instrument lumens, and/or any other suitable distal element. These image receiving windows (examples of which are shown in FIGS. 5 and 6) may be equipped with an objective lens for a fiberscope, or an image pick-up device for an electronic scope, such as a charge-coupled device (CCD). The image receiving windows receive an image from the distal end of flexible shaft 14. The received image may be transmitted to operating unit 15 by an image guide of a fiberscope or lead wire of an electronic scope, which may be inserted into flexible shaft 14, and then transferred through universal cord 19. A light guide such as an optical fiber, inserted in the bore of light projecting windows (examples of which are shown in FIGS. 5 and 6) may run through operating unit 15 via universal cord 19, and may be connected to a light source outside. The light source then may project light from the distal end surface of the light guide.

Figure 4:
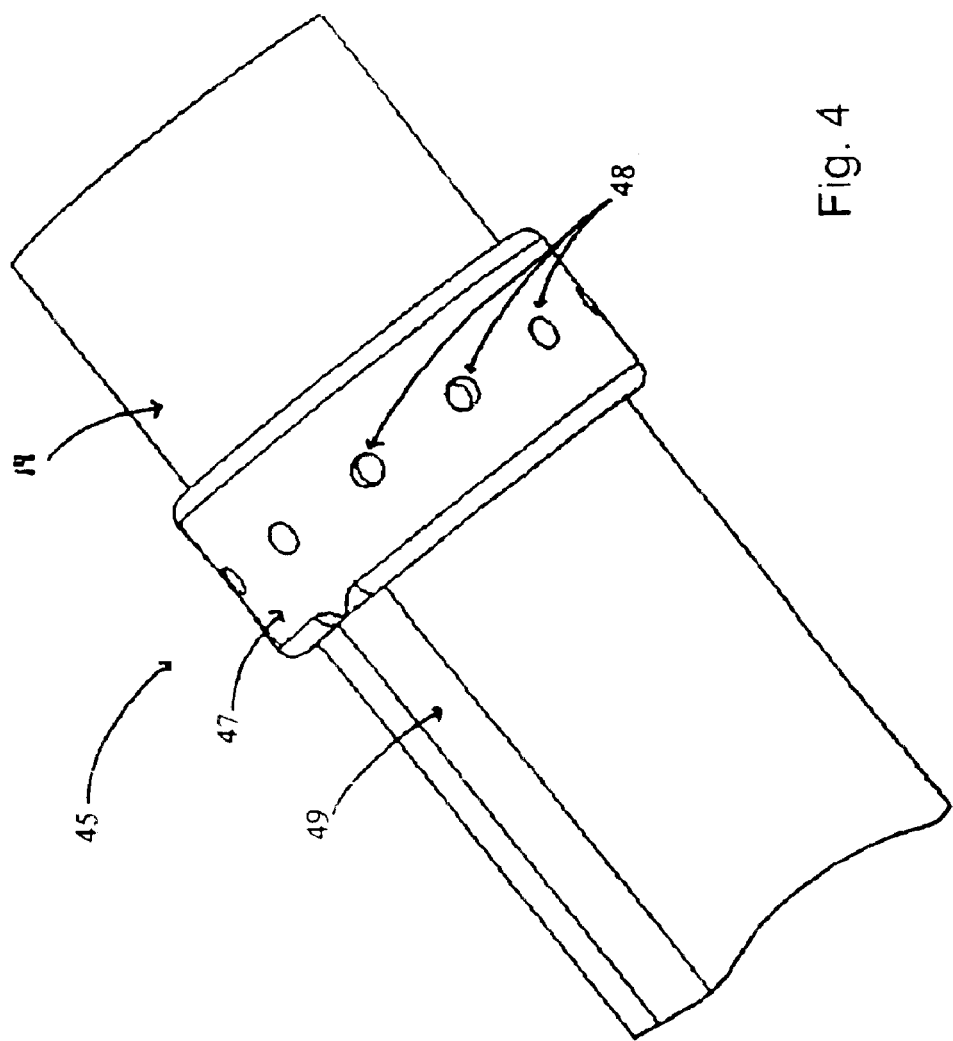
FIG. 4 illustrates a further embodiment of an anesthetic collar for delivering fluid to a patient's gastrointestinal tract in accordance with the present invention.

Instrument lumens (examples of which are shown in FIGS. 5 and 6) may be connected to an instrument insertion opening 17 at operating unit 15 so that instrument 20 may be inserted through flexible shaft 14. Instrument 20 may be a snare, forceps, a suction tube, an RF probe, or other suitable instrumentation. Endoscope 10 further comprises delivery nozzle 16, which may be connected with fluid lumens (examples of which are shown in FIGS. 4, 5 and 6). Endoscope 10 illustrates one embodiment of endoscope 10, however it is contemplated that colonoscopes, EGD scopes, cystoscopes, and other suitable scopes may be used with the present invention.

FIG. 2A illustrates one embodiment of anesthetic collar 25, where anesthetic collar 25 comprises annulus 26, lumen 28, and adapter 29. Anesthetic collar 25 is adapted for placement on flexible shaft 14. Annulus 26 may be a band that circumnavigates or partially encircles flexible shaft 14. Annulus 26 may be constructed from rubber, plastic, composites, and/or any other suitable material that may be safely used within the human body. Annulus 26 is, in one embodiment of the present invention, an enclosed chamber having a hollow core (not shown), external surface 32, and expulsion pores 27 in external surface 32. Annulus 26 may include any suitable number of expulsion pores 27. Expulsion pores 27 may be configured in any suitable way to permit desirable fluid coverage of the gastrointestinal tract. Annulus 26 may be adapted to contain fluid such as, for example, a 0.1% Lidocaine solution, where the fluid may be expelled through expulsion pores 27 into the gastrointestinal tract of a patient. Annulus 26 may be coupled to lumen 28, where lumen 28 may be any suitable conduit capable of delivering fluid to annulus 26. Lumen 28 is coupled to annulus 26 in a manner that permits the free flow of fluid from lumen 28 into the hollow core of annulus 26.

In the particular embodiment shown in FIG. 2A, lumen 28 extends distally from annulus 26 to a distal section 11 of flexible shaft 14, where lumen 28 is coupled to adapter 29. Adapter 29, in one embodiment of the present invention, is adapted to removably couple with an existing lumen of flexible shaft 14. An example of such a lumen would be an instrument insertion lumen. Adapter 29 may be inserted into the existing lumen, where adapter 29 may be secured by any suitable means such as, for example, a friction fit. Adapter 29 is designed to permit the free transfer of fluid pumped through the existing lumen of flexible shaft 14 into lumen 28 and annulus 26, where fluid pumped into annulus 26 may then be expelled through expulsion pores 27 into the gastrointestinal tract of the patient.

Anesthetic collar 25 may be permanently affixed or detachably coupled to flexible shaft 14. When detachably coupled, anesthetic collar 25 may be held to flexible shaft 14 by an adhesive, a high friction coefficient, shrink fit, heat shrink tubing, heat shrink fit, threaded section, and/or by any other suitable coupling means. Anesthetic collar 25 allows lubricants, local anesthetics, dyes, and/or other desirable fluids to be passed through the existing lumen of flexible shaft 14 into annulus 26, where the fluid may be distributed through expulsion pores 27 into the gastrointestinal tract. Utilizing the existing lumens found in endoscopes, the present invention allows those fluids that may reduce the pain and discomfort associated with endoscopies such as, for example, local anesthetics and lubricants, to be distributed in an even fashion throughout the gastrointestinal tract, where such fluids may reduce the drug level requirements for sedative and analgesic agents. Placing anesthetic collar 25 towards the distal end 11 of flexible shaft 14 may allow anesthetic fluids passing through anesthetic collar 25 to take effect as more proximal portions of flexible shaft 14 bend around uncomfortable flexures such as the splenic flexure and come into contact with nerve endings in the gastrointestinal tract. Further, the removable embodiment of the present invention permits the easy removal of anesthetic collar 25 for the sterilization and cleaning of endoscope 10 (FIG. 1). Distal end 11 may house any suitable endoscopic component such as, for example, one or a plurality of instrument insertion lumens, light projecting windows, image receiving windows, and fluid lumens.

Still referring to FIG. 2A, anesthetic collar 25 may be placed at any suitable location on flexible shaft 14. A plurality of anesthetic collars may be used, where multiple collars coupled to an existing lumen of flexible shaft 14 may be used to disperse desirable fluids at a plurality of locations. Fluid may be dispensed through the existing lumen of flexible shaft 14 by a fluid pump, manual injection, or by any other suitable means. Further embodiments of anesthetic collar 25 comprise constructing annulus 26 from a porous material in the absence of expulsion pores 27, where fluid pumped into annulus 26 may ooze through the porous outer surface. The present invention further comprises designing anesthetic collar 25 with any suitable dimensions, shapes or profiles; adhering anesthetic collar 25 to the distal section 11 of flexible shaft 14; providing a plurality of lumens branching from adapter 29 to annulus 26; and/or any other suitable configuration in accordance with the present invention.

Figure 2B:
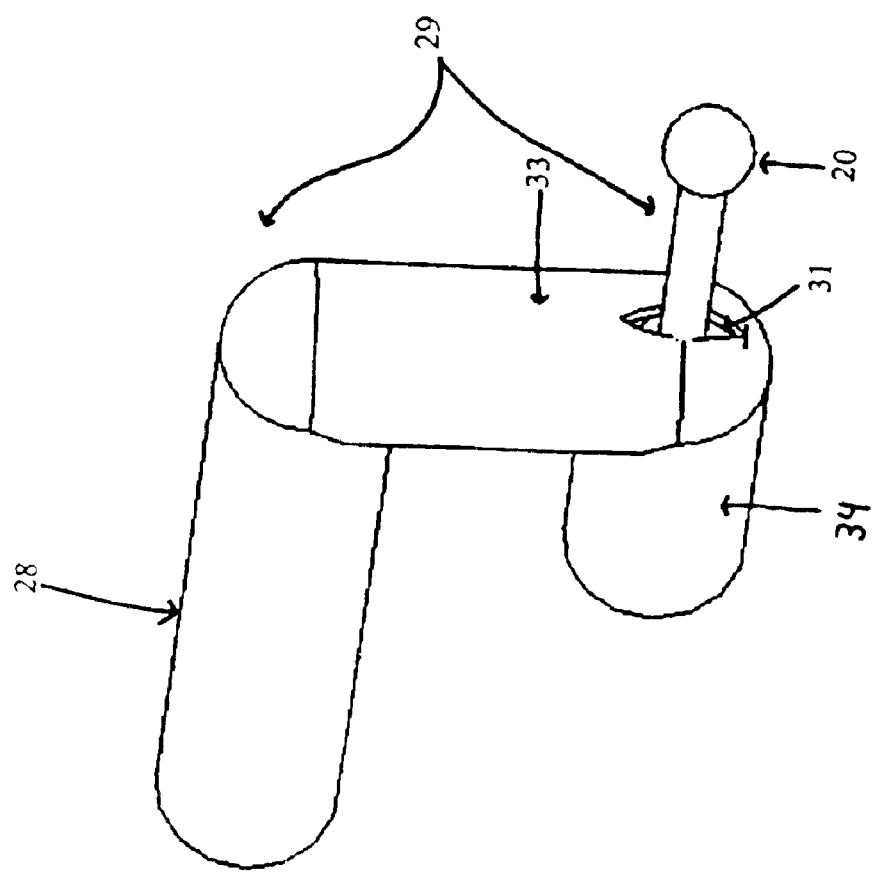
FIG. 2B illustrates a further embodiment of an adapter for an anesthetic collar in accordance with the present invention.

FIG. 2B illustrates an alternate embodiment of lumen 28 and adapter 29, where adapter 29 comprises ascending portion 33 and transverse portion 34. Transverse portion 34 may be substantially collinear with and coupled with an existing lumen of flexible shaft 14 (FIG. 2A). Ascending portion 33 may connect transverse portion 34 with lumen 28, where lumen 28 may be integrated with annulus 26 (FIG. 2A). Ascending portion 33 further comprises an aperture 31, which may be a slit in ascending portion 33. In one embodiment of the present invention, adapter 29 is constructed from a pliable material such as a plastic or rubber. Instrument 20 may be passed through an existing lumen of shaft 14, through transverse portion 34, and out through aperture 31. Instrument 20 may push apart the sides of aperture 31 to pass through, however, when instrument 20 is removed, aperture 31 may retain a substantially water tight seal.

When the use of instrument 20 is desired to perform polypectomies or other medical procedures, instrument 20 may be inserted into flexible shaft 14 until it protrudes through slit 31. When instrument 20 is no longer needed, it may be removed from flexible shaft 14, whereupon aperture 31 may return to a watertight seal. Once instrument 20 has been removed, desirable fluids such as lubricants and local anesthetics may be dispensed through the existing lumen of flexible shaft 14, through transverse portion 32, through ascending portion 33, through lumen 28, and into annulus 26 (FIG. 2A). The substantially watertight seal of aperture 31, when instrument 20 is not present, may allow fluid to be dispensed through annulus 26 rather than simply out the distal section 11 of flexible shaft 14. The illustrated embodiment of aperture 31 allows for the use of instruments and the delivery of desirable fluids to take place through a single lumen. The illustrated embodiment may take advantage of existing lumens within flexible shaft 14 without compromising a clinician's ability to insert an instrument at any desirable time. Aperture 31 may be a valve, a flap affixed to a hinge, or any other suitable means of permitting instrumentation to pass through ascending portion 33. It is further contemplated that fluid may be dispensed through an existing lumen of flexible shaft 14 simultaneously with the use of an instrument inserted through the same lumen.

Figure 3:
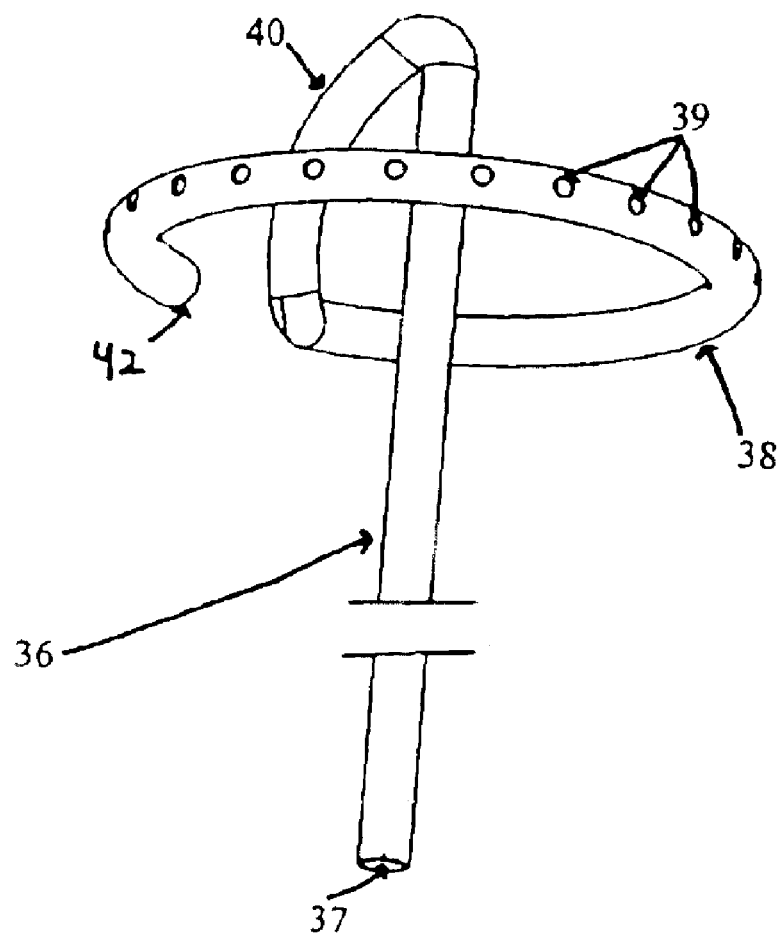
FIG. 3 illustrates one embodiment of an insertion member for insertion into an endoscope in accordance with the present invention.

FIG. 3 illustrates one embodiment of an insertion member 35, where insertion member 35 comprises a lumen 36, a descending portion 40, and a band portion 38. In one embodiment of the present invention, lumen 36 is flexible and may be straightened for insertion into an existing lumen of flexible shaft 14 (FIGS. 1 and 2A). An example of such a lumen would be an instrument insertion lumen described below with respect to FIG. 5. Lumen 36 is further designed to extend from a fluid delivery mechanism, such as a fluid pump or manual fluid injection assembly, coupled with proximal end 37. Insertion member 35 may be driven through an existing lumen in flexible shaft 14 until lumen 36 is able to exit the existing lumen distally and take the form illustrated in FIG. 3. Descending portion 40 and band portion 38 may be constructed from memory retention material such that descending portion 40 and band portion 38 may take their illustrated shape once they have passed through the distal opening of the existing lumen. The descending portion 40, for example, may extend proximally with respect to flexible shaft 14, where band portion 38 may then encircle flexible shaft 14 proximal to distal section 11 (FIG. 1).

As shown in FIG. 3, band portion 38 may further comprise closure 42. Closure 42 may be any suitable seal or closure means that prevents fluid from escaping from the end of lumen 36. Band portion 38 further comprises expulsion pores 39. Fluid pumped through lumen 36 may pass through expulsion pores 39 into the gastrointestinal tract. Lumen 36 may be used to deliver local anesthetics, lubricants, dyes, and/or other desirable fluids. Furthermore, insertion member 35 may be inserted into and removed from the existing lumen of flexible shaft 14 at any time during a medical procedure allowing other instrumentation to be inserted into the existing lumen as needed. The present invention further comprises configuring insertion member 35 with any suitable dimensions and shapes that allow for the efficient and comprehensive delivery of fluids to the gastrointestinal tract. For example, insertion member 35 may include multiple band portions, multiple descending portions, a descending portion having expulsion pores in the absence of a band portion, or any other suitable configuration.

FIG. 4 illustrates one embodiment of an anesthetic collar 45, where anesthetic collar 45 comprises annulus 47 and lumen 49. Anesthetic collar 45 is adapted for placement on flexible shaft 14 (FIGS. 1 and 2A). Annulus 47 may be a band that circumnavigates flexible shaft 14 or partially encircles flexible shaft 14, where annulus 47 may be constructed from rubber, plastic, composites, and/or any other suitable material that may be safely used within the human body. Annulus 47, in one embodiment of the present invention, is an enclosed chamber having a hollow core (not shown), where the external surface of annulus 47 has expulsion pores 48. Annulus 47 comprises any suitable number of expulsion pores 48, which may be configured in any suitable way to permit comprehensive fluid coverage of the gastrointestinal tract. Annulus 47 may be adapted to deliver fluid such as, for example, a 0.1% Lidocaine solution, where the fluid may be expelled through expulsion pores 48 into the gastrointestinal tract of the patient. Annulus 48 may be coupled to lumen 49, which may be any suitable conduit capable of delivering fluid to annulus 47. Lumen 49 is coupled to annulus 47 in a manner that permits the free flow of fluid from lumen 49 into the hollow core of annulus 47. In one embodiment of the present invention, lumen 49 extends from annulus 47 proximally towards operating unit 15 (FIG. 1), where lumen 49 may be coupled with, for example, a fluid pump or manual fluid injection assembly. Lumen 49 may be secured to flexible shaft 14 by an adhesive, covered in a sheath, or secured by any other suitable coupling means.

Anesthetic collar 45 may be permanently affixed or detachably coupled to flexible shaft 14. When detachably coupled, anesthetic collar 45 may be held to flexible shaft 14 by an adhesive, by creating a high coefficient of friction, heat shrink tubing, shrink fit, heat shrink, threaded section, and/or by any other suitable coupling means. Anesthetic collar 45 allows lubricants, local anesthetics, dyes, and/or other desirable fluids to be passed through the existing lumen of flexible shaft 14 into annulus 47, where the fluid may be distributed through expulsion pores 48 into the gastrointestinal tract.

The embodiment of FIG. 4 is well suited for use with an endoscope that does not have an internal lumen available for fluid delivery. Utilizing existing lumens secured to (e.g., FIG. 4) or found in (e.g., FIG. 6) flexible shaft 14, the present invention allows those fluids that may reduce the pain and discomfort associated with endoscopies such as, for example, local anesthetics and lubricants, as well as fluids that may be helpful in diagnosing patients, such as dyes, to be distributed in an even fashion throughout the gastrointestinal tract. Placing anesthetic collar 45 towards the distal section 11 of flexible shaft 14 may allow anesthetic fluids passing through anesthetic collar 45 to take effect and ease patient discomfort as more proximal portions of shaft 14 bend around uncomfortable flexures such as the splenic flexure and come into contact with nerve endings in the gastrointestinal tract. Further, the removable embodiment of the present invention permits the easy removal of anesthetic collar 45 for the sterilization and cleaning of endoscope 10 (FIG. 1).

Still referring to FIG. 4, the present invention comprises placing anesthetic collar 45 at any suitable location on flexible shaft 14 as well as the use of a plurality of anesthetic collars, where multiple collars coupled to an existing lumen of flexible shaft 14 may be used to disperse desirable fluids at a plurality of locations. Fluid may be pumped through the existing lumen of flexible shaft 14 by any suitable means such as, for example, an automatic fluid pump or a manual fluid injection assembly. Further embodiments of anesthetic collar 45 comprise constructing annulus 47 from a porous material in the absence of expulsion pores 48, where fluid pumped into annulus 47 may ooze through the porous outer surface. The present invention further comprises designing anesthetic collar 45 with any suitable dimensions, adhering anesthetic collar 45 to the distal section 11 of flexible shaft 14, providing a plurality of lumens coupled to annulus 47, and/or any other suitable configuration in accordance with the present invention.

FIG. 5 illustrates a cross-sectional view of one embodiment of distal end 11 of flexible shaft 14 (as shown in FIG. 1) in accordance with the present invention, where flexible shaft 14 comprises image receiving window 53, instrument lumen 52, fluid lumen 54, light projecting window 56, and outlet lumens 55. Lumen 52 may be a multi-purpose instrument lumen, where a clinician may insert instruments such as forceps, biopsy needles, and snares through instrument insertion opening 17 (FIG. 1), down lumen 52, and out through distal section 11 (FIG. 1). Fluid lumen 54 comprises a lumen or other suitable fluid delivery means that extends from delivery nozzle 16, or from any other suitable fluid insertion point, towards the distal section 11 of shaft 14. Fluid lumen 54 may open at distal section 11 of flexible shaft 14 or may be sealed at any point along flexible shaft 14.

Outlet lumens 55 of flexible shaft 14 may radiate from fluid lumen 54, may run substantially perpendicular to, or at any suitable angle from, fluid lumen 54, and may open through outer surface 57. In one embodiment of the present invention outlet lumens 55 are cylindrical, yet any other suitable lumen form or cross-section capable of fluid delivery is contemplated. The present invention further comprises outlet lumens of any suitable diameter for delivering fluid from fluid lumen 54 to the gastrointestinal tract of a patient. As fluid is pumped through fluid lumen 54, the fluid will encounter outlet lumens 55, where fluids may pass through the outlets into the gastrointestinal tract of the patient. In one embodiment of the present invention, outlet lumens 55 extend radially from fluid lumen 54; however, any suitable configuration of outlet lumens 55 may be used with the present invention. For example, the outlet lumens (or set of lumens as in FIG. 4) may be positioned serially or longitudinally, where outlet lumens are exposed through outer surface 57 at intervals along the length of flexible shaft 14. Likewise, flexible shaft 14 may be suitably configured in a number of ways in accordance with the present invention. For example, flexible shaft 14 may have one or a plurality of lumens 52, one or a plurality of image receiving windows 53, one or a plurality of fluid lumens 54, and/or any number of other suitable additions.

Fluid lumen 54 allows local anesthetics, lubricants, dyes and/or other suitable fluids to be passed through shaft 14 and into the gastrointestinal tract without comprising instrument lumen 52 and blocking image receiving window 53. Further, placing outlet lumens 55 towards the proximal end of flexible shaft 14 may allow such fluids to cover a broad surface area of tissue, where as local anesthetics take effect, more proximal portions of shaft 12 may cause less pain and discomfort to the patient as they pass through the gastrointestinal tract.

FIG. 6 illustrates a cross-sectional view of a further embodiment of annulus 26 in accordance with the present invention, where annulus 26 circumnavigates flexible shaft 14. In the illustrated embodiment, flexible shaft 14 comprises image receiving window 61, instrument insertion lumen 62, light projecting lumen 68, fluid lumen 63, and fluid port 64. Fluid lumen 63 may be a lumen or other suitable fluid delivery means that extends from delivery nozzle 16 (FIG. 1), or from any other suitable fluid insertion point, towards the distal section 11 of shaft 14. Delivery nozzle 16 may be coupled with any suitable fluid delivery system such as, for example, a fluid pump or a manual fluid injection assembly. Fluid port 64 is an offshoot of fluid lumen 63 that allows fluid to pass from fluid lumen 63 into annulus 26. Fluid port 64 obviates the need for additional lumens and/or adapters, such as those shown in FIG. 2A, for example, because annulus 26 (forming part of anesthetic collar 25) can be placed directly over fluid port 64 of flexible shaft 14. Fluid port 64 may have any suitable dimensions or configurations that facilitate the movement of fluid between fluid lumen 63 and annulus 26.

Annulus 26 may be permanently affixed or detachably coupled to shaft 14, where annulus 26 is aligned with fluid port 64 in order to allow fluid to pass into the hollow core of annulus 26. Once fluid has passed into annulus 26 from fluid port 64, the fluid will be expelled from annulus 26 through expulsion pores 66 into the gastrointestinal tract. Fluid port 64 may be located anywhere and at more than one location along the length of flexible shaft 14, preferably near distal section 11.

Figure 7:
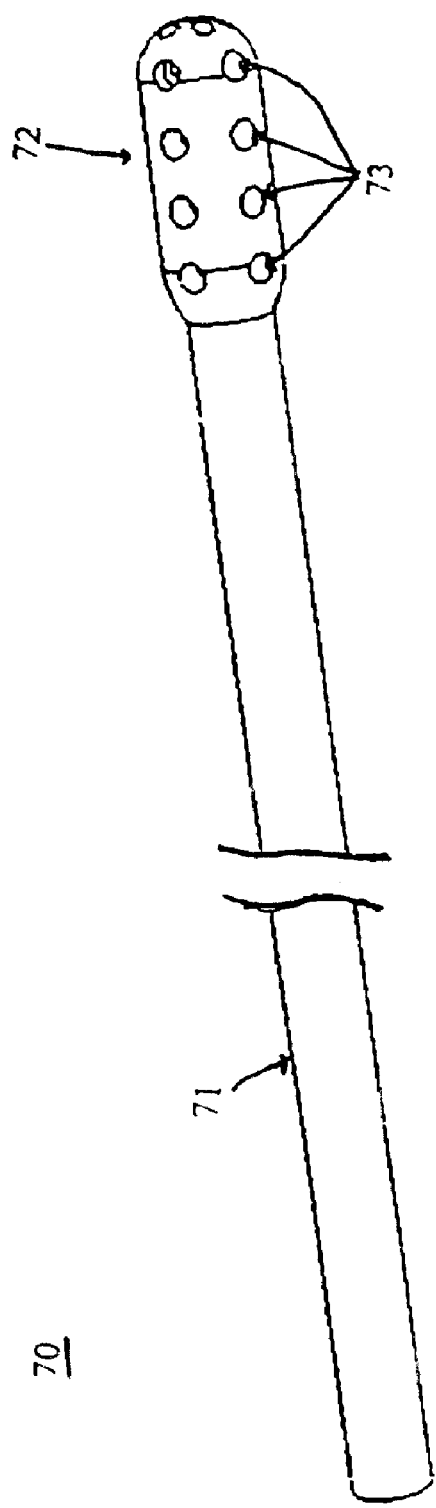
FIG. 7 illustrates a further embodiment of an insertion member in accordance with the present invention.

FIG. 7 illustrates one embodiment of an insertion member 70, which comprises lumen 71, head 72, and expulsion pores 73. In one embodiment of the present invention, lumen 71 is flexible and may be inserted into an existing lumen such as, for example, instrument insertion lumen 52 (FIG. 5) of flexible shaft 14 (FIG. 1). Lumen 71 is further designed to extend from a fluid delivery mechanism such as, for example, a fluid pump or a manual fluid injection assembly, coupled with proximal end 73, through an existing lumen in flexible shaft 14 until lumen 71 is able to exit the existing lumen at the distal section 11 of flexible shaft 14. Insertion member 70 may deliver fluids such as local anesthetics, dyes, and lubricants to the gastrointestinal tract of a patient, where fluid passing through lumen 71 enters head 72 and is expelled through expulsion pores 73. Head 72 may be a hollow chamber positioned at the distal most point of lumen 71, however any suitable design that facilitates the comprehensive dispersion of fluids into the gastrointestinal tract is in accordance with the present invention. For example, head 72 may be spherical, elliptical, or have any other suitable form, where one or a plurality of expulsion pores 73 may be positioned in any suitable configuration on head 72. Insertion member 70 may be constructed from any material suitable for use within the human body, however, the preferred embodiment comprises the construction of insertion member 70 from flexible material such as, for example, plastic, rubber, or composites.

The present invention allows clinicians to insert insertion member 70 into flexible shaft 14 at any point during an endoscopic procedure, where insertion member 70 may be used to deliver local anesthetics, lubricants, dyes, and/or other suitable fluids to the gastrointestinal tract. The removable nature of insertion member 70 allows the clinician to extract insertion member 70 if the existing lumen is needed for the insertion of other instrumentation or if the delivery of fluids is no longer needed. The plurality of expulsion pores 73 found on head 72 in one embodiment of the present invention allows fluids to be distributed in a comprehensive manner in order to affect a large surface area of tissue. By affecting a large surface area of tissue, the present invention may effectively lubricate and/or anesthetize such tissue in order to diminish the pain and/or discomfort experienced by the patient during the procedure.

Figure 8:
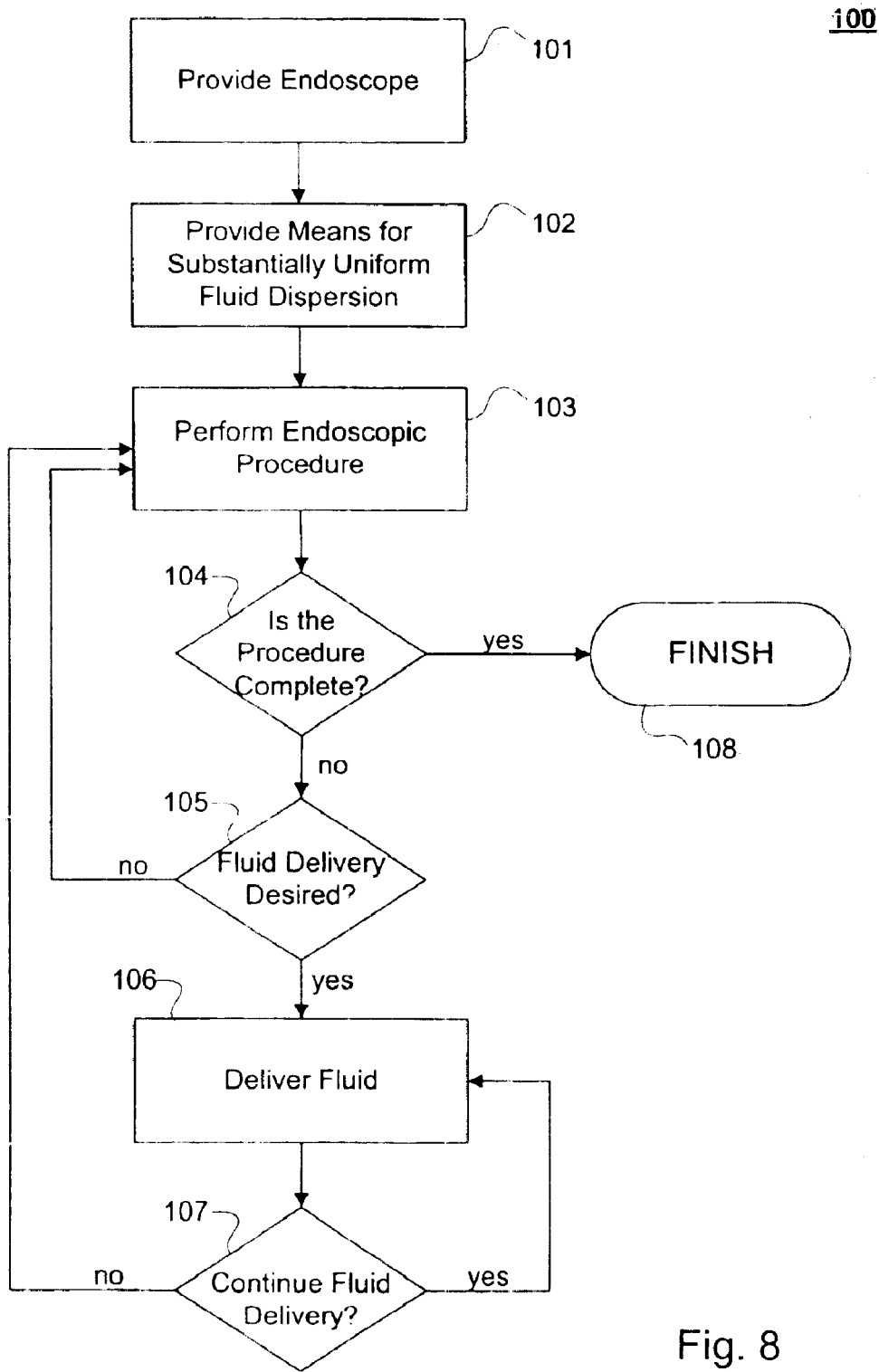
FIG. 8 illustrates one embodiment of a method for delivering fluid endoscopically to a patient in accordance with the present invention.

FIG. 8 illustrates one embodiment of a method 100 for delivering fluids to the gastrointestinal tract of a patient. Method 100 comprises step 101 for providing an endoscope such as, for example, endoscope 10 (FIG. 1), however other suitable scopes may be used. Step 102 of method 100 comprises providing a fluid delivery means, where the fluid delivery means may be anesthetic collar 25 (FIG. 2A), anesthetic collar 45 (FIG. 4), insertion member 35 (FIG. 3), insertion member 70 (FIG. 7), embodiments of flexible shaft 14 as depicted in FIG. 5, embodiments of flexible shaft 14 and annulus 26 as depicted in FIG. 6, and/or any other suitable fluid delivery means for providing substantially uniform fluid dispersion. Step 102 further comprises coupling the fluid delivery means to flexible shaft 14 (FIG. 1) when necessary, providing the fluid delivery means, where the fluid delivery means may be an insertion member, and/or otherwise preparing the fluid delivery system.

Step 103 of method 100 comprises performing the endoscopic procedure, where the procedure may be, for example, a colonoscopy. Step 103 further includes preparing the endoscope for insertion, inserting the endoscope into the patient, and performing any suitable procedure with the endoscope. Step 103 may include performing the procedure without the administration of fluids. However, query 105 of method 100 may take place before the endoscope is inserted to ensure that fluids may be delivered at any desirable time during the procedure. Query 104 of method 100 comprises ascertaining whether the endoscopic procedure is complete, where procedures may be performed in the total absence of fluid delivery, however, this capability may be present at all times. If the procedure is complete, method 100 may transition to finish 108, where finish 108 indicates a fully completed procedure including the extraction of the endoscope. If the procedure is not complete, method 100 may transition to step 105.

Step 105 comprises ascertaining whether fluid delivery is desired. If fluid delivery is not desired, method 100 may loop back to step 103, where the procedure may continue without the additional delivery of fluids. If fluids are desired, method 100 may proceed to step 106. Step 106 comprises delivering fluids through the fluid delivery means of step 102 into the gastrointestinal tract of the patient. Fluids include, but are not limited to, dyes, local anesthetics, and lubricants. Fluids may also be defined to include gases, where gases may be administered through the fluid delivery means to the gastrointestinal tract of the patient. During fluid delivery, method 100 may continue to perform the endoscopic procedure of step 103, where fluid delivery in accordance with step 106 may be administered while the procedure is taking place. Query 107 may continually ascertain whether fluid delivery is desired, where method 100 may loop back to step 103 if fluid is no longer desired.

The illustrated method allows for fluids to be delivered to the gastrointestinal tract of a patient at any point during a procedure depending on the needs of the clinician. Fluid delivery may further be halted and restarted at any desirable points during the procedure. Such fluids may decrease the pain and/or discomfort commonly associated with a number of endoscopic procedures. Further, fluids such as dyes may be used for diagnostic purposes independent of or in cooperation with pain reducing fluids. The present invention further comprises the delivery of gases, irrigation water, suction, and/or any other feature that may be suitably performed in accordance with the present invention.

While exemplary embodiments of the invention have been shown and described herein, it will be obvious to those skilled in the art that such embodiments are provided by way of example only. Numerous insubstantial variations, changes, and substitutions will now be apparent to those skilled in the art without departing from the scope of the invention disclosed herein by the Applicants. Accordingly, it is intended that the invention be limited only by the spirit and scope of the claims as they will be allowed.

What is claimed is:

1. A system for providing gastrointestinal pain management during an endoscopic procedure, comprising:
   an endoscope comprising an operating unit and a flexible shaft that includes at least one lumen; and
   an anesthetic collar comprising an annulus, wherein said anesthetic collar is adapted for placement on said flexible shaft so as to permit free transfer of a fluid through said at least one lumen of said flexible shaft to said annulus and wherein said annulus comprises an enclosed chamber having a hollow core and one or more expulsion pore to permit fluid flow into the gastrointestinal tract of a patient.

2. The system of claim 1, wherein said anesthetic collar further comprises an additional lumen and an adapter, said adapter being coupled to both said at least one lumen and said additional lumen.

3. The system of claim 1, wherein said fluid comprises at least one of local anesthetics and lubricants.

4. The system of claim 1, wherein said fluids are distributed in an even fashion throughout said gastrointestinal tract.

5. The system of claim 1, wherein said anesthetic collar is permanently affixed to said flexible shaft.

6. The system of claim 1, wherein said anesthetic collar is detachably coupled to said flexible shaft using at least one of an adhesive and friction, shrink, heat shrink, and threaded fit.

7. The system of claim 1, further comprising at least one additional anesthetic collar.

8. The system of claim 1, further comprising a fluid pump to dispense fluid through said lumen of said flexible shaft.

9. The system of claim 1, wherein said adapter includes an aperture with a substantially watertight seal such that an instrument can be passed through said lumen of said flexible shaft and through said aperture to access the gastrointestinal tract of a patient.

10. The system of claim 1, wherein said annulus comprises porous material to allow said fluid to seep through to said gastrointestinal tract in the absence of said expulsion pores.

11. An anesthetic collar for providing gastrointestinal pain management during an endoscopic procedure, comprising:
   an annulus including an enclosed chamber having a hollow core and discharge means so as to permit discharge of fluid from the enclosed chamber through the annulus; and
   means for securing said annulus to a flexible shaft of an endoscope.

12. The system of claim 11, further comprising an adapter connected to said annulus, wherein said adaptor is coupled to at least one lumen extending substantially along the length of said flexible shaft so as to permit free transfer of a fluid through said at least one lumen to said annulus and wherein said anesthetic collar is adapted for placement near the distal end of an endoscope's flexible shaft.

13. The anesthetic collar of claim 12, further comprising an additional lumen connecting said annulus to said adaptor.

14. The anesthetic collar of claim 12, wherein said at least one lumen is an existing lumen internal to said flexible shaft.

15. The anesthetic collar of claim 12, wherein said at least one lumen is secured to the exterior of the flexible shaft.

16. An apparatus for providing gastrointestinal pain management during an endoscopic procedure comprising:
   a lumen extending from a fluid delivery mechanism, wherein said lumen is capable of being inserted through an internal tubular cavity along a flexible shaft of an endoscope and passing beyond the distal end of said shaft; and
   a head comprising a plurality of expulsion pores, wherein said head is connected to the distal end of said lumen so as to allow free flow of fluid from said lumen through said expulsion pores so as to facilitate comprehensive dispersion of said fluids into a patient's gastrointestinal tract.

17. The apparatus of claim 16, wherein said apparatus is flexible and can be inserted through an endoscope's flexible shaft.

18. The apparatus of claim 16 wherein said head further comprises a band portion connected to said lumen and encircling said flexible shaft.

19. The apparatus of claim 18, wherein said band portion is made of memory retention material.

20. A flexible shaft for an endoscope for providing fluids during an endoscopic procedure, comprising:
   an image receiving window;
   a light projecting window;
   an instrument lumen for passing instruments related to endoscopic procedures into said patient's gastrointestinal tract;
   a fluid lumen extending along the length of said flexible shaft so as to permit free transfer of a fluid; and
   one or more outlet lumens connected to said fluid lumen and arranged such that said fluid passing through said fluid lumen is distributed in an even fashion throughout the path of travel of said flexible shaft.

21. The flexible shaft of claim 20, wherein said one or more outlet lumens is located generally near the distal end of said shaft.

22. A method for delivering fluids to the gastrointestinal tract of a patient during an endoscopic procedure, comprising:
   providing an endoscope comprising a flexible shaft;
   providing a fluid delivery means, wherein the fluid delivery means may be one of an anesthetic collar, an insertion member, and a fluid lumen and outlet lumens integrated into said flexible shaft;
   preparing the endoscope for insertion;
   inserting the endoscope into the patient;
   ascertaining whether fluid delivery is desired; and
   delivering fluids through said fluid delivery means into the gastrointestinal tract of said patient.

23. The method of claim 22, further comprising coupling the fluid delivery means to said flexible shaft.

24. The method of claim 22, wherein said fluids comprise at least one of dyes, local anesthetics, lubricants and gases.

* * * * *